United States Patent [19]
Andersson et al.

[11] Patent Number: 5,440,496
[45] Date of Patent: Aug. 8, 1995

[54] PROCEDURE AND APPARATUS FOR PRODUCING INDIVIDUALLY DESIGNED, THREE-DIMENSIONAL BODIES USABLE AS TOOTH REPLACEMENTS, PROSTHESES, ETC.

[75] Inventors: Matts Andersson, Lerum; Lennart Carlsson, Mölndal; Erik Isberg, Ellös, all of Sweden

[73] Assignee: Nobelpharma AB, Goteborg, Sweden

[21] Appl. No.: 217,761

[22] Filed: Mar. 25, 1994

Related U.S. Application Data

[63] Continuation of Ser. No. 805,955, Dec. 12, 1991, abandoned.

[30] Foreign Application Priority Data

Dec. 12, 1990 [SE] Sweden .................................. 9003967

[51] Int. Cl.[6] ........................ G01B 11/00; G05B 19/00
[52] U.S. Cl. .................................. 364/474.05; 33/504; 364/474.03
[58] Field of Search ..................... 364/474.04, 474.05, 364/474.24, 474.06, 474.03, 550, 551.01, 551.02, 559, 560, 561, 562, 563; 356/376, 380; 33/503, 504, 505, 23.01-23.09

[56] References Cited

U.S. PATENT DOCUMENTS

| | | | |
|---|---|---|---|
| 4,084,244 | 4/1978 | Floter | 364/474 |
| 4,394,608 | 7/1983 | Tryber et al. | 318/578 |
| 4,575,805 | 3/1986 | Moermann et al. | 364/474 |
| 4,663,720 | 5/1987 | Duret et al. | 364/474.05 |
| 4,742,464 | 5/1988 | Duret et al. | 364/474.05 |
| 5,003,484 | 3/1991 | Vollmayr | 364/474.03 |
| 5,027,281 | 6/1991 | Rekow et al. | 364/474.05 |
| 5,092,022 | 3/1992 | Duret | 364/474.05 |
| 5,184,306 | 2/1993 | Erdman et al. | 364/474.05 |
| 5,193,282 | 3/1993 | Aramaki et al. | 33/23.01 |
| 5,204,824 | 4/1993 | Fujimaki | 364/474.03 |
| 5,224,049 | 6/1993 | Mushabac | 364/474.05 |
| 5,283,509 | 2/1994 | Matsuura et al. | 318/577 |
| 5,313,400 | 5/1994 | Tsukamoto | 364/474.03 |

FOREIGN PATENT DOCUMENTS

WO15376 12/1990 WIPO.

Primary Examiner—Roy N. Envall, Jr.
Assistant Examiner—Brian C. Oakes
Attorney, Agent, or Firm—Pollock, Vande Sande & Priddy

[57] ABSTRACT

A method for producing at least one three-dimensional body. Conditions for sensing at least one model are preset. The conditions includes at least an angle of at least one sensor with respect to a longitudinal axis of the model and a relationship between a rotation speed of the model and a speed of movement of the sensor and the model relative to each other in a direction parallel to the longitudinal axis of the model. The model is rotated while simultaneously moving at least one of the model and the sensor relative to each other in a direction parallel to the longitudinal axis of the model while simultaneously sensing a plurality of distances generated by interaction between the sensor and a surface of the model to obtain a first set of data. The preset conditions and the first set of data are transmitted to at least one control for controlling at least one working tool for producing the three-dimensional body. The preset conditions of the at least one sensor and the at least one model substantially duplicated for at least one working tool and at least one blank respectively. The three-dimensional body is produced by varying a position of the working tool relative to the blank corresponding to the sensed distances generated by interaction between the sensor and the model, such that the working tool selectively removes material from the blank to substantially reproduce the surface of the model on the blank.

19 Claims, 4 Drawing Sheets

PROCEDURE AND APPARATUS FOR PRODUCING INDIVIDUALLY DESIGNED, THREE-DIMENSIONAL BODIES USABLE AS TOOTH REPLACEMENTS, PROSTHESES, ETC.

This application is a continuation of Ser. No. 07/805,955 filed on Dec. 12, 1991 now abandoned.

FIELD OF THE INVENTION

The present invention relates to a procedure for producing individually designed, three-dimensional bodies intended to form at least parts of artificial replacements for teeth, dental bridges and joints; support parts for reconstruction of tissue build-up; and tools for producing whole or parts of such replacements and support parts, and the like. The present invention also relates to an apparatus for implementation of the above procedure.

BACKGROUND OF THE INVENTION

Using the procedure and apparatus according to the present invention, it will thus be possible to manufacture both an implant body and a tool part or parts employed in the production of the implant body. Production of a tool part for an implant body is relevant to the production of tooth sockets whose inner configuration must be adaptable with extreme accuracy to the tooth remains in question. In this case, electro-erosion is employed, in which it is necessary that the outer configuration of the tool part coincide with extreme accuracy (100 parts of 1 mm) with the outer configuration of each respective tooth remain. In such instance, it should also be noted that the tool parts (which, in the case of production of tooth crowns, consist of electrodes of graphite) are exposed to wear (primarily frontal wear) during the electro-erosion. The production of a tool part or parts is also relevant in the procedure for producing ceramic bodies which are linearly enlarged in relation to the replacement or support part and reduced in size by hard sintering in order to conform with extreme accuracy to the size of the replacement or the support part.

It is previously known in this art to transfer a configuration from a model to the implant body or the tool part herefor. By way of example, reference is made to the tracer milling cutter according to PCT application SE87/00194 WO 87/06451). This tracer milling cutter employs a sensing needle which senses the configuration of the model in question, and hydraulically operating servo devices which transfer the movements sensed by the needle to the processing tools which form the blank. The above-mentioned publication discloses in general terms that it is possible to alternatively employ a tracer milling cutter which operates with electric servo devices.

It is also previously known in the art to propose, in the above type of tracer milling cutter, an apparatus which makes possible enlargement/reduction of the form of a sensed model.

It is also well known in the art to employ electro-erosion in the production of, for instance, tooth crowns/tooth sockets.

The prior art equipment imparts an extremely high degree of accuracy to the produced implant bodies which are usually characterized by unique, individual outer and/or inner configurations.

It is also previously known in the art to attempt to cast the individually shaped bodies. Casting of such bodies provides inferior surfaces and requires individually designed and shaped tools. This mode of approach must be regarded as inferior to the principles according to the present invention which are based on cutting or some other type of forming machining.

In the production of implant bodies, there is a general need to be able to rationalize production of such implant bodies which must then be capable of displaying individually distinguished and also complex inner and/or outer configurations. The prior art equipment and procedures for this purpose are relatively slow, and in certain cases require the production of bodies of advanced design which cannot be achieved, or which can be achieved only with difficulty, using today's prior art equipment.

There is also a need in the art for increase in access to biocompatible material in connection with replacements and implant of support bodies in the human body. As a rule, such material is difficult to work with and must be capable of being employed in cost-effective and manufacture-efficient procedures and apparatus for the production of organic forms.

Hence, there is a need in the art to technically simplify the machines employed and their associated equipment, while still being able to utilize these more generally in the production of implant bodies. In this instance, the purely hydraulically operating equipment suffers from limitations and requires a relatively large machine park if all-round production of individual bodies and electro-erosion tools for these were to be satisfied. Different machines are thus required for cases with or without enlargement/reduction function. Production of tooth sockets and tool parts for these also requires other machine, since the tool parts must be designed with a wear allowance. The production of, for instance, complete teeth requires an additional machine variant. Those cases in which it is desired to build onto the produced form in relation to the form of the sensed model (as may be relevant in the production of a complete tooth/tooth part), would theoretically require one kind of machine for each superstructure operation, which, in principle, would be impossible to satisfy with present-day hydraulically operated tracer milling cutters.

The ideal is thus to be able to utilize a single machine in which it is possible to manufacture the desired implant body in response to controls which may be simply varied. In this instance, it must be possible to enter information on the configuration of the body in question either manually or automatically by read-off, copying, and the like, whereafter the control equipment generates, in response to such information, the correct control signals to the machine which, in response to the generated control signals, produces the usually individually shaped body.

The hydraulically operating tracer milling cutter also suffers from drawbacks of not being capable of working sufficiently rapidly. The sensing needle must abut against the model with a certain force, the so-called reaction force. The model is usually made of a plaster of Paris or other soft material, which limits the magnitude of the reaction force. On the other hand, the reaction force must be increased with increasing working speed in order for the needle to be capable of following the contour, and the above-mentioned limitation in working speed will be readily perceived herefrom. In addition, the needle must be provided with a rounded tip (not a spiculated tip) in order for the model/plaster material not to be destroyed by the needle. This limits sensing accuracy in complicated shapes and it will readily be perceived that implant bodies of complex individual shapes cannot, for this reason, be manufactured with a sufficient degree of accuracy. The possibility of producing the implant body with complex shapes is also restricted by the fact that the axes of rotation of the rotary units cannot work above the rotary shaft of the blank because the above-mentioned axes of rotation are inclined at an angle in relation to each other. Such angular setting affords a number of advantages which it would be difficult to forego in the above-mentioned prior art tracer milling cutter.

The procedure and the apparatus according to the present invention are also intended to make possible the production of cavities in relevant blanks with a high degree of accuracy.

SUMMARY OF THE INVENTION

The object of the present invention is to propose a method and an apparatus which obviates at least the major part of the above-outlined drawbacks. al, that identification is included of one or more shapes on one or more of the above-mentioned bodies. In addition, a first respective digital representation of each respective identification is to be formed. Each respective first digital representation is provided in a storage and processing unit/computer. This hardware handles, for example by file and/or database processing, each respective first digital representation. This handling may possibly include the application, preferably via a terminal, of at least one piece of information with which actuation may be effectuated, for example shape change, size change, etc. and the like, in relation to each respective first representation with its respective information, in addition to which the generation of at least one second representation which differs from the relevant first representation may thus be realized in response to the above actuation. The storage and processing unit is activated to accomplish one or more read-outs via one or more output ports of one or more of the first representations and one or more of the second representations, where applicable. Devices, switch actuators, positioning devices etc. which are included in one or more machines for production using one or more of the above-mentioned read-outs are controllable by means of each respective read-out or read-outs. Each respective actuator is actuated depending on its control in an actuation function where a blank and members acting thereon are brought into co-ordination with one another of the device by means of the relevant read-out, allocating to allocating to the blank the relevant read-out shape. Such actuation in relation to the first representation may be achieved by means of the above-mentioned second representation and/or change, for example, additional change, in identification, machine setting, and the like. In identification, additional change may thus be added, while in machine setting, adjustment or change of "errors" in the processing may be modified.

In one embodiment, one or more models are produced of the above-mentioned bodies, identification being optionally executed with the aid of the shape or shapes of the model or models. Supplementary information or alternatively a description may be produced for each respective form of each respective model or body, and identification be effectuated with the aid of such description. The description may thus comprise description parts which respectively indicate co-ordinates, for example read-off angle of the body during read-off and position in a co-ordinate system for each respective read-off or plotting point. In one embodiment, use is made in the description of for the shape build-up. These significances may consist of predetermined codes characteristic of the build-up of the shape which form abbreviations or representations, hereinafter designated third representations, of or for the complete description parts. The information mass produced with the codes will, by such means, be considerably reduced in relation to the information mass of the complete description parts. The codes may be stored in the processing units (its host or associated memory), in which also these complete first and second representations are generated with the aid of codes on each respective deposition or loading occasion to the machine or machines.

In one embodiment, first and second data are entered regarding a second shape associated with the model, the read-off or the copying, or possible differences in relation to the first shape in dimension and/or configuration which are to be present for the second shape in the memory hardware associated with the computer device, for example in the form of a PC, microprocessor, and the like, which in turn is included in or connected to an electric control unit in which the above-mentioned controls are generated in the form of electric control signals. Furthermore, the novel procedure is characterized in that the electric control signals are based on/calculated in the computer hardware from relevant data of the above-mentioned first and second data and are fed to the movement-effectuating device which, in this instance, includes an electrically controlled servo device, switch actuator, and the like, whose movement effectuation is executed by utilization of a slight inertia resistance in the movement-effectuating devices.

In an additional further development of the novel procedure according to the present invention, first information by means of which the above-mentioned first data may be generated is retrieved by a copier, for example, a dentist, a dental technician, and the like, and transmitted by means of computer transfer or storage media to a central host unit which controls the production of implant bodies, and, at the central host unit, the above-mentioned first data is entered into the above-mentioned electric control unit/computer hardware on the basis of the first information. The computer transfer media may then preferably consist of a transmission line, for example a hooked-up and/or permanent connection in the general telecommunications network. Transmission and reception devices which preferably include modems are connected or connectible to the above-mentioned transmission line for transmission of the first information.

The data regarding of different percentages in enlargement and reduction of the shape, different changes of the second shape in relation to the first shape, and the like, are entered into the above-mentioned memory/computer hardware. The second data is selected for each respective production case, by means of actuation of terminal devices associated with or connected to the computer hardware. The rotary units are, or one of the rotary units is, controlled by the electric control unit to achieve an optimum production time in respect of machining speed and accuracy. In such instance, each respective longitudinally displaceable rotary unit is longitudinally displaced depending on the degree of complexity of the first shape. In such first portions of the first shape as represent a first part shape which permits a certain first maximum machining speed, each respective unit is longitudinally displaced at the first maximum machining speed. In such second portions of the first shape as represent a second part shape which permits a certain second maximum machining speed which differs from the first maximum machining speed, each respective unit is longitudinally displaced at the second maximum machining speed, and so on.

Further embodiments of the novel procedure according to the present invention are apparent from the appended description.

The novel apparatus according to the present invention is, among other things, characterized in that identification means are provided for identifying one or more shapes of one or more of the above-mentioned bodies. Means are also provided for forming a first digital representation of each respective identification. A storage and processing unit (computer) is operative to receive each respective first digital representation. The storage and processing unit is further operative to handle each respective first digital representation. Such handling may comprise set-up in a file or files or in a database or databases. The handling may also include the possible application (performable from a terminal associated with the storage and processing unit) of at least one item of information for actuation, for example shape change, size change, and the like in relation to each respective first representation with each respective item of information and generation of at least one second representation which differs from the relevant first representation in response to the above-mentioned actuation. The storage and processing unit is further operative to make possible read-out via one or more associated output ports, of one or more of the first representations and possibly one or more of the second representations, if applicable. Switch actuators/positioning devices are provided and are controllable by means of one or more of the read-outs. These devices are actuated in response to their controls in an actuation function in which a blank and one of the devices acting thereof are brought in to co-ordination as a result of the actuation of the device by means of the relevant read-out, and in which the blank is, by such means, allocated the relevant read-out shape. The novel apparatus may also be characterized in that, in cases where the above-mentioned actuation in relation to the first representation is to be present, such actuation is realized with the aid of the above-mentioned second representation and/or change which, in this instance, may consist of an additional change, in identification, machine setting, and the like.

In one embodiment, the device generating the control signals includes an electric control unit which, in turn, comprises or is connected/connectible to computer means, such as a PC, microprocessor, etc., in whose associated memory equipment first and second data may be entered regarding a second shape associated with the model, the read-out or the copy, or a difference in relation to the first shape in dimension and/or form which is to be present for the second shape. In addition, the apparatus is characterized in that the control unit generates, depending on relevant data on the above-mentioned first and second data, electric signals to the movement-effectuating device which, in this instance, includes or consists of an electrically controlled servo device, switch actuator, with slight inertia resistance.

In yet a further embodiment, the apparatus is characterized in that the electric control unit is included in a distribution system for the transfer of first information by means of which the above-mentioned first data may be generated in the memory equipment/computer hardware. This distribution system includes, on the one hand, a number preferably a plurality, of initiation or gathering stations for the first information, and, on the other hand, computer storage and/or computer transmission devices for the first information from these stations to a central or host station including the electric control unit and the memory equipment/computer hardware. The first items of information are converted into the first data in the memory equipment/computer hardware in connection with the transfer of the first items of information to the main station or, after intermediate storage or holding in the main station. The computer transmitting devices include transmitter and reception devices and transmission communication between the above-mentioned transmitting and receiving station. The transmission communications preferably include permanent and/or hook-up connections in the general telecommunications network, to which the transmitter and reception devices are connected/connectible.

In one preferred embodiment, the electric control unit is arranged to control one or both of the blank and tool supporting units for their mutual longitudinal displacement movements at speeds which are dependent upon the degree of complexity of the first shape, for example, in complex shape portions of the first shape at a first speed, in less complex shape portions of the first shape at a second speed which exceeds the first speed, and so on.

In such first shapes or in such part portion of the first shape in which the machining device cannot operate above the axis of rotation of the blank because of the overall configuration of the first shape, the electric control unit controls each respective rotary unit so that machining in a given phase takes place during parts of a rotation turn for each respective rotary unit.

In one embodiment, the apparatus includes two or more pairs of rotary units in which each respective pair is included in its allocated machine or machine equipment part. In this instance, the electric control unit controls directly, or via sub-control units, the different unit pairs/machines/machine equipment parts on the basis of the same first shape/model/read-off/copy. A first pair of blank and tool-supporting units/a first machine/a first machine equipment part then shape a first blank which forms or is to form the implant body and which has an outer configuration corresponding to the outer configuration of the model, the read-off or the copy, or has been allocated the difference in relation to the outer configuration of the model/the read-off, or the copy. At least second and third pairs of blank and tool-carrying units/second and third machines/second and third machine equipment parts shape second and third blanks which form first and second tool parts in the form of electro-erosion devices intended for producing an inner shape of the implant body which then obtains a socket shape in its final form (such as a tooth crown). The first tool part forms a rough production tool part which has been provided with frontal wear durability for compensating frontal wear in the electro-erosion. The second tool part forms a fine production tool part with close approximation to the second shape.

In one embodiment, the blank and tool-carrying units carry the blank and the processing device, respectively, with rigidly journalled shafts with a slight overhang between the part carrying the blank and the part carrying the processing device, respectively, and a shaft bearing/an immediately proximal shaft bearing.

As a result of the present invention, the processing time in the machine may be shortened five to ten times of the time it takes to manufacture the implant body using the prior art tracer milling cutter. And yet, the principle of processing or correspondingly shaping manufacture can still be employed. The machine park may be simplified and more complex shapes may be produced with the same degree of accuracy as previously applied to simpler shapes in employing the tracer milling cutter. Handling for transfer of model information or the like from the dentist/dental technician to the manufacturing unit may be considerably reduced and, for instance, it will be possible to utilize information transfer instead of physical package mailing in a simple manner via the public telecommunications network. Technical accuracy data with respect to the individual nature of the object is established by the dentist/dental technician, while superstructure parts/superstructure functions to the body may be applied by processing of data in the computer hardware on the basis of tests or experience. Different tests and experiments may, in each respective individual case, be conducted in order to obtain fully satisfactory results. The manufacturing process may be individually adapted to the transmitting stations and the resources of the main central station. In exact copying, for example, no other data need be employed. A number of machines can simultaneously be utilized for, for example, tooth crown production in which the production of the implant body proper is performed in a first machine, and graphite electrodes for subsequent electro-erosion can be produced in other machines. Enlargement and reduction functions of the produced body in relation to the model may be performed by simple pushbutton operations or manual activation. The overall throughflow time for an implant body can thus be substantially reduced. Alternatively, one or a few machines may be employed to produce bodies and for programmings. The procedure and the apparatus are suitable for different types of chipforming machining, for example cutting machining, laser machining, and the like.

The division of the sensing and machining functions of the mechanical tracer milling cutter into different locally placed units affords the above advantages in flexible production and machine park composition.

BRIEF DESCRIPTION OF THE ACCOMPANYING DRAWINGS

One currently proposed embodiment of an apparatus and a procedure performed using the apparatus will be described in greater detail hereinbelow, with particular reference to the accompanying Drawings, in which.

DETAILED DESCRIPTION OF THE PREFERRED EMBODIMENT

Figure 1:
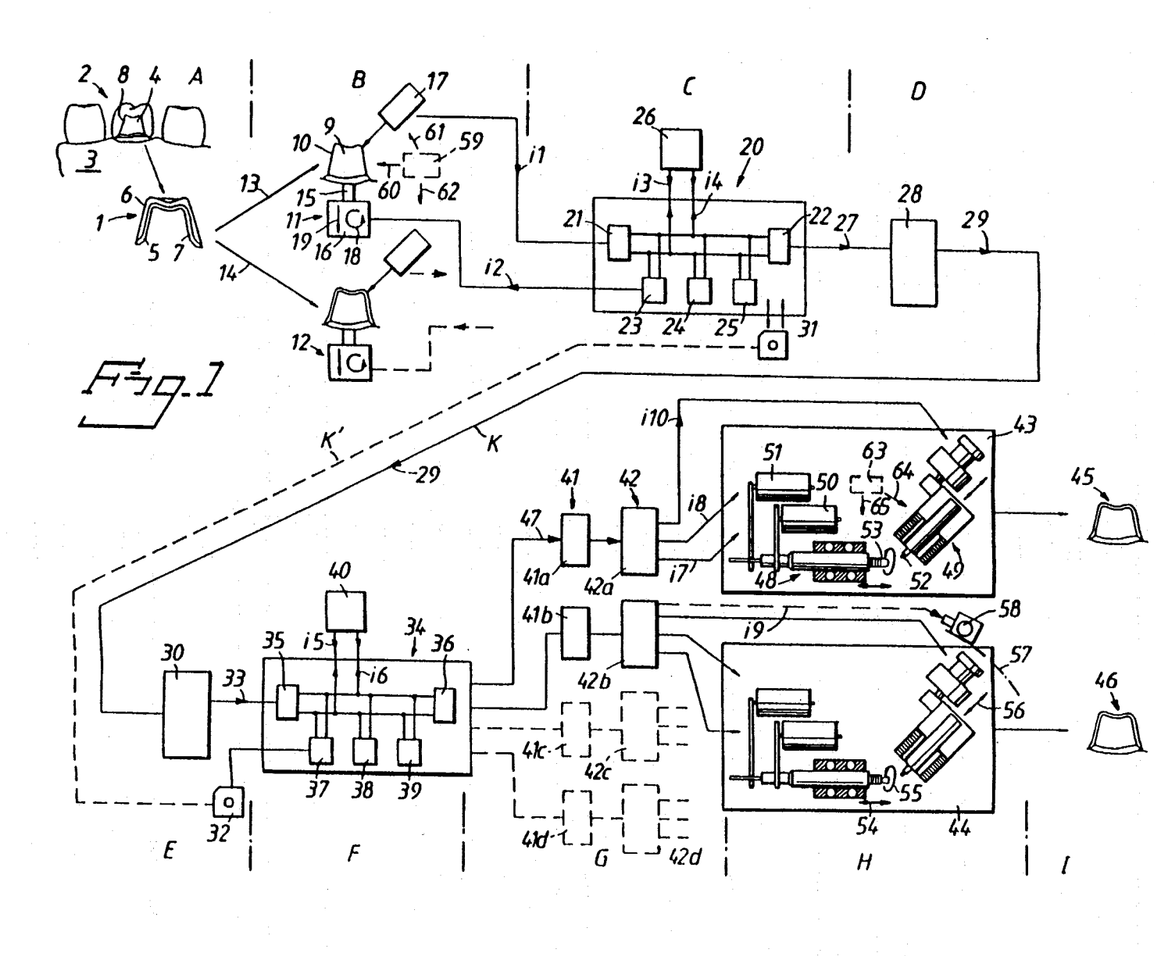
FIG. 1 schematically illustrates the production of three-dimensional implant bodies for living organisms.

In FIG. 1, a number of sub-stations are indicated by reference letters A–I. In station 1 which is located at a dentist, doctor or other examiner, a model 1 is produced from, for example, a tooth 2 in a jaw 3. The model forms a prepared tooth which has been built up from a tooth remain 4 in the jaw. This model is produced by a model-producer (dentist, doctor, and the like) The model includes a metal or ceramic shell 5 and material 6 applied on this shell. The model includes an inner form 7 which corresponds to the outer form 8 of the tooth remain 4. From the model, a positive model 9 is produced which thus corresponds to the outer form 8 of the tooth remain 4. This positive model 9 is utilized in a second station B in which a read-off, description, identification, and the like is performed of the outer form 10 of the positive model. The positive model is disposed on or in read-off equipment 11 which may be of different type and operating principle. In FIG. 1, two principles are represented by reference numerals 11 and 12. The transfer from station A to station B is symbolized by arrows 13 and 14, respectively. The model 9 is disposed on a bracket 15 and can, by means thereof, be applied to the read-off device 11 which, in the illustrated case, comprises a rotary and displacing device 16. Moreover, the sensing device 11 includes a unit 17 sensing the form 10, this unit also being optionally designed or constructed on the basis of different principles. Rotation of the model 9 is symbolized by the arrow 18 and displacement by the arrow 19. By rotating and displacing the model 9 in a predetermined manner with simultaneous sensing of the surface 10 by means of the unit 17, a mathematical representation can be obtained with the aid of read-off signals i1 and control signals i2. The read-off signals depart from the unit 17 and the control signals i2 are impressed upon the rotary device 16. The sensing device 12 is controlled in a corresponding manner by means of the above-mentioned signals.

One station C includes a storage and processing unit 20 which may consist of a personal computer. Such a personal computer may be purchased on the open market. The personal computer comprises input and output ports 21 and 22. In addition, a CPU 23 is included, and memory devices 24, 25. A terminal 26 is provided for entering information i3 and accessing information i4. The above-mentioned control signal i2 is controlled from the CPU of the computer 20. The accessed information i1 is entered and received in the computer where the information is stored and processed. The accessed information from the unit 17 is obtained preferably in digital form, even though analog read-off may be carried out and converted into digital information in the computer. With the aid of the signals i1 and i2, there is thus generated for each respective read-off form 10, a first digital representation of each respective identification. The digital representation which is created as a result of the sensing is stored in memory devices 24 and/or 25. The personal computer handles the above-mentioned representation and sets this up in a a file or files or a database or databases. The information i3 is possibly entered for modification, such as form change, size change, and the like, in relation to the first representation, with each respective item of information i3 and generation of at least a second representation which differs from the relevant first representation depending on the above-mentioned modification. The computer unit 20 is actuable for read-out of one or more of the above-mentioned representations and one such read-out is indicated in FIG. 1 as 27. The read-out 27 is transmitted to a station D which includes modem means 28 utilized for transferring the read-out on a line K permanently connected and/or connectible to the public telecommunications network. The digital signal departing from the modem is indicated by numeral 29. This signal 29 is received in a receiver station E which includes a receiver modem 30 which is adjusted into harmony with the modem 28 and the communication line K. Such a data transfer effectuated by the modems 29 and 30 may consist of known type. By way of example, mention may be made that the "DATEL" leased line service can be utilized. Since the principles of this type of service are well known, they will not be described in greater detail here, it being merely ascertained that it operates with frequency shift keying and conforms with CCITT recommendations. Alternatively, the read-off 27 may be obtained on a diskette which may be loaded into and unloaded from the computer 20 and on which the read-out 27 may thus be transferred. This diskette may be transferred by an alternative route K' (by post) to the station E where the diskette has been represented by numeral 32. The communication K is preferably of the type which effectuates series communication.

The memories 24, 25 in the computer 20 may consist of primary and secondary memories. The information regarding the outer form 10 of the model 9 produced in the computer may be arranged in a file or database. Such files or databases are entered in the secondary memory. The file or database contents, respectively, can be transferred to the working memory (the primary memory). Formation/editing of additional file or files, or data contents which represent varying or form-modified information items of the first information may be carried out with the aid of the second information item i3 and the file and database contents, respectively, which represent the outer form 10 of the model 9. The thus produced additional files or database contents, respectively may also be entered in the secondary memory. Hence, the read-outs 27 may represent both read-off form and modified form. Such editing may be performed using a processing form which operates on the basis of graphics. On the screen (not shown in detail) of the terminal 27, a graphic representation can in such instance be obtained. As file or database processing, use may be made of known protocol, and in this instance, mention may be made of the so-called transfer protocol PCPIP (U.S. navy) for file or database processing. On transfer from the secondary memory to the working memory, a processing program is activated which may consist of a conversion program which draws broken lines, angles, and the like with the aid of the information in the file or the database contents, respectively. By way of example of such programs, mention might here be made of POSTSCRIPT (for terminals), GKS (Graphic Kernel System) which effectuates editing of the additional files or data contents, respectively. GKS is a so-called editor.

A receiver station F of the information 33 received from the modem 30 (or the diskette 32) includes a second computer 34 of a design corresponding to that of the computer 20. This computer also includes input and output ports 35 and 36, respectively. Moreover, a CPU 37 is included, and secondary and primary memories 38 and 39, respectively. The computer 34 also includes a terminal 40 via which information i5 may be applied, and information i6 may be read off. The computer 34 controls the memory and control devices 41 and 42, respectively, which are included in a processing station G. The processing station in turn controls a machine park H which may comprise one or more machines 43, 44. In the machine park, the relevant individual bodies 45, 46 are manufactured which consist of implant bodies, support bodies, tools, and the like. These bodies 45, 46 are finally treated in a station I which may include electro-erosion processes, material application processes, and the like. In this embodiment, a memory 41a, 41b, 41c, 41d is each allocated, by the memory units, 41, their control unit 42a, 42b, 42c and 42d, respectively. Each control unit 42 is then allocated to its machine/machine set. Thus, the unit 42a is allocated the machine 43, unit 42b the machine 44, and so on. Information 47 which is current on each occasion for execution by each respective machine 43, 44 is transferred from the computer 34 to the memories 41. Control of each respective machine is performed by each respective control unit 42. The items of information 47 to the memory and control units can be performed on BUS communication of a known type (for example HE's BUS communication). Each respective control unit provides, for each respective machine, those sequences, movement patterns, and the like which are relevant in each machine.

Each respective machine includes a blank-carrying unit 48 and a tool-carrying unit 49, these units 48 and 49 being described in greater detail hereinbelow.

The blank-carrying unit is rotated by means of a motor 50 and is longitudinally displaced along its longitudinal axis by means of a motor 51. The tool-carrying unit is disposed to cause its pertinent processing tool 52 to abut, during ongoing processing, against the blank 53 rotated and longitudinally displaced by the unit 48. The longitudinal displacement movement of the unit 48 is disclosed by reference 54 and the rotational movement by reference 55. The longitudinal displacement movements of the unit 49 are indicated by reference No. 56. As will be apparent from the horizontal view according to FIG. 1, the longitudinal axes of the units 48 and 49 are disposed at an angle with respect to one another. In a more detailed embodiment (not shown), this angle may be varied with the aid of a symbolically shown gear rim 57 which carries the unit 49. With the aid of a motor 58, the gear rim 57 is rotated and the above angle between the units 48 and 49 can be varied by such means with the aid of a control signal to the motor 58. The control units 42 generate the signals to the motors 50, 51 and 58 and to a switch actuator/positioning device/electric servo included in the unit. In FIG. 1, a control signal to the motor 50 is indicated by reference i7, a control signal to the motor 51 by i8, a control signal to the motor 58 by i9, and a control signal to the device by i10.

The read-off form 10 of the model 9 can thus be modified if desired. Such modification information can be entered at different points in the identification and production chain. It is, thus, possible to apply to the model 9 a foil of a given thickness which then may represent the form modification. Similarly, the read-off function using the unit 17 may be influenced in the desired manner such that an enlargement of the form 10 takes place. Actuations such as these have been symbolized by a part 59 and arrows 60, 61 and 62. Actuation for modification may also be performed in station C with the aid of the second information i3. Such actuation for form modification, enlargement, and the like may also be performed in station F with the aid of the information i5. The above-mentioned actuation for form modification, enlargement, and the like may also be performed in the machines 43, 44. In this case, the modification is realized in that the error of the machine is adjusted manually and/or electrically. Such actuation has been symbolized in FIG. 1 by the cart 63 and the arrows 64 and 65. The equipment illustrated in FIG. 1 operates largely as follows. A model is produced in station A. One or more forms of the model or model 9 deriving from the model are sensed in station B with the aid of sensing equipment controlled from a computer in station C. This latter computer also prepares protocols/files/databases on such sensing. The stored information is possibly processed, and the information from stored or processed representations is read out from the computer unit. This read-out may be performed on command from the personal computer and/or on command from subsequent equipment. The read-out is transmitted via modem in the telecommunications network or its equivalent. The read-out is transferred via a communication connection to which receiver equipment is connected in a station E. The received information is stored and possibly processed in a station F which includes a computer unit which, in turn, controls memory and control units in a subsequent station G. The receiver units E and F may basically be connected to a plurality of stations A–D and, conversely, the stations A–D may be connected to different stations E–H (I). In this latter case, different tool parts and bodies may be made at geographically separate sites. For instance, sockets may be manufactured at one site, tools at another site, and so on. The computers 20 and 34 in the stations C and F can form master and slave relationships vis-á-vis one another. Information in a computer can be in another computer. The computer 34 may, for example, give priority to accessed information from a plurality of computers 20, and manufacture body/tool for information with the highest priority. The control unit 42 contains basic data for the basic functions of the machine park 43, 44, and data/information is fed to the memories 41 which is valid for each respective manufacturing occasion. Read-out and entry of information in the memory and control units may be performed from the computer 34.

Figure 2:
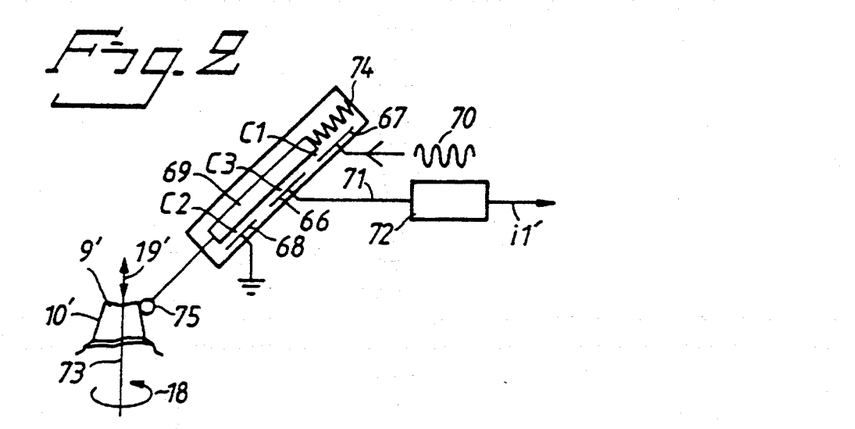
FIG. 2 schematically illustrates a first embodiment of apparatus for read-off or sensing of a configuration of a three-dimensional body.
Figure 3:
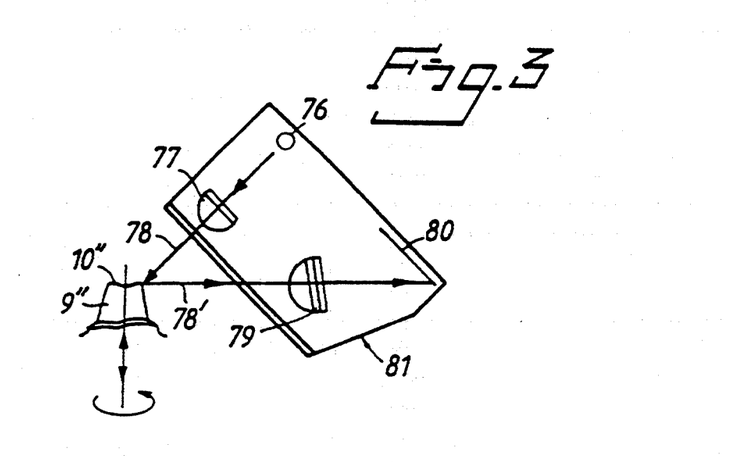
FIG. 3 schematically illustrates a second embodiment of the apparatus for sensing a configuration of a body.

FIGS. 2 and 3 each show their read-off principle, the principle illustrated in FIG. 2 relating to so-called capacitative indicators, and the principle according to FIG. 3 taking place by optical means. The capacitative indicator according to FIG. 2 fundamentally includes three permanent electrodes 66, 67 and 68, and one electrode 69 displaceable depending on the sensed form. Three capacitors may thus be considered as existing, namely one capacitor C1 between the electrodes 67 and 68, one capacitor C2 between the electrodes 68 and 69, and one capacitor C3 between the electrodes 66 and 69. The electrode 67 is connected to a frequency 70 which may be of of about 1 mHz. The voltage caused by the frequency will be divided up between the capacitors C1 and C2 in relation to their inherent capacitances. The variation will be performed in response to the longitudinal displacement position of the displaceable electrode in relation to the electrode 67 and 68. The capacitance of the capacitor C is constant over the measurement area because of the fact that the electrode 66 is constantly covered by the electrode 69. At one connection terminal 71 to the electrode, it will thus be possible to sense a voltage which exists on the electrode 69 at each respective relevant position, and this voltage will always be proportional to the longitudinal displacement of the electrode 69. In one embodiment, the electrodes may be designed as cylinders in which the electrodes 66, 67 and 68 are thoroughly insulated from one another and the electrode 69 is in the form of a rod of conductive material which is displaceable within the cylinders. The indicator is connected to an electric converter which gives the digital representation i1' on its output (see FIG. 1). The displaceable rod 69/the electrode extends towards the model 9' and abuts against the outer form 10' of the model. The above-mentioned sensing takes place depending on the rotation 18' of the model about the longitudinal axis 73 and the longitudinal displacement 19' along the longitudinal axis 73. The electrode or rod 69 is urged against the model 9' by means of a counter spring 74 which may actuate the sensing device 75 towards the surface of the model 9' with a predetermined abutment force.

The sensing principle according to FIG. 3 operates by so-called non contact sensing of the triangulation type using laser light. In this case, a laser source 76 is included, as well as light emitting means 77. The departing laser beam 78 is reflected against the surface 10" of the model 9". The model 9" is rotated and longitudinally displaced along its axis of rotation in a manner corresponding to that of FIG. 2. The surface 10" reflects the laser light 78 and the reflected light has been indicated by reference 78'. The unit includes receiver means 79 (lens) which refracts the impinging light towards a detector surface 80. The detector (not shown in detail) emits signals in response to the angles of the incoming light 78'. By such means, a digital signal corresponding to the form can be generated on the output of the unit 81 (see FIGS. 1 and 2). This type of indicator is commercially available in a plurality of makes and, by way of example, mention may be made of the indicator from Nippon Automation CO LTD, Japan, of the type "Laser Analog Sensor LAS 5010". Fundamentally, the indicator operates such that a light beam is generated by the light source 76 and is focussed by an optical system 77 against the surface 10". The spot arising on the surface is observed by the detector 79, 80 consisting of optics 79, a detector surface 80 and a positional-sensing circuit (not shown in detail), such as a so-called CCD detector (CCD=Charge Coupled Device). Such circuits are well-known in the art and will not be described in greater detail here.

Figure 4:
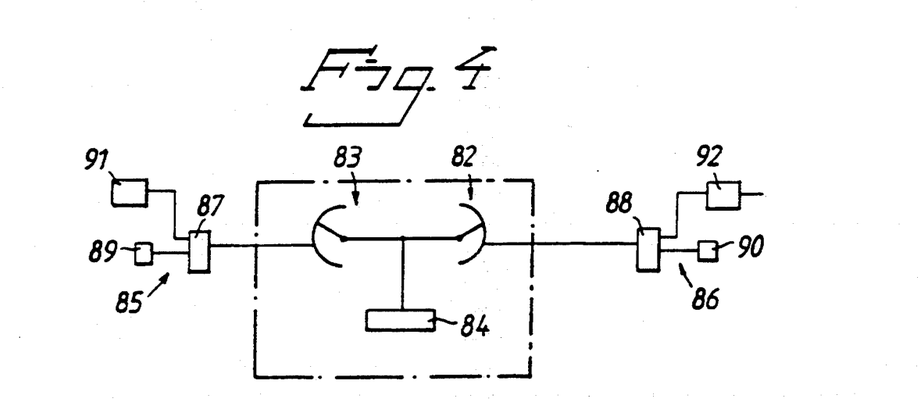
FIG. 4 schematically illustrates the information transfer via the telecommunications network of information from a sensing and storing side to a receiving and processing side.

In FIG. 4, reference 82 indicates a telecommunications system in which the selector matrix has been symbolized by reference 83 and control means (register etc.) by reference 84. The transmitting and receiving sides 85 and 86, respectively, are connected to the telecommunications system 82 as subscribers. Each respective subscriber installation 85, 86 includes a modem 87, 88 (see 28, 30 in FIG. 1). Each respective installation may include telephone sets 89 and 90, respectively, and connections of PCs 91 and 92, respectively, or corresponding storage and processing devices (see the computers 20 and 34 in FIG. 1).

Figure 5:
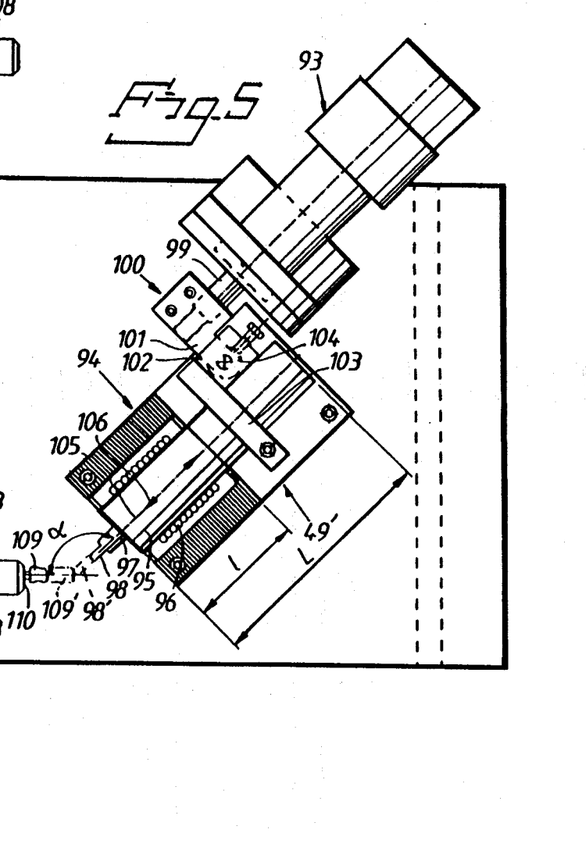
FIG. 5 is a horizontal view showing one embodiment of a blank-supporting unit and a tool-supporting unit, the units being mutually longitudinally displaceable along their longitudinal axes which, in this instance, are angled in relation to each other.
Figure 6:
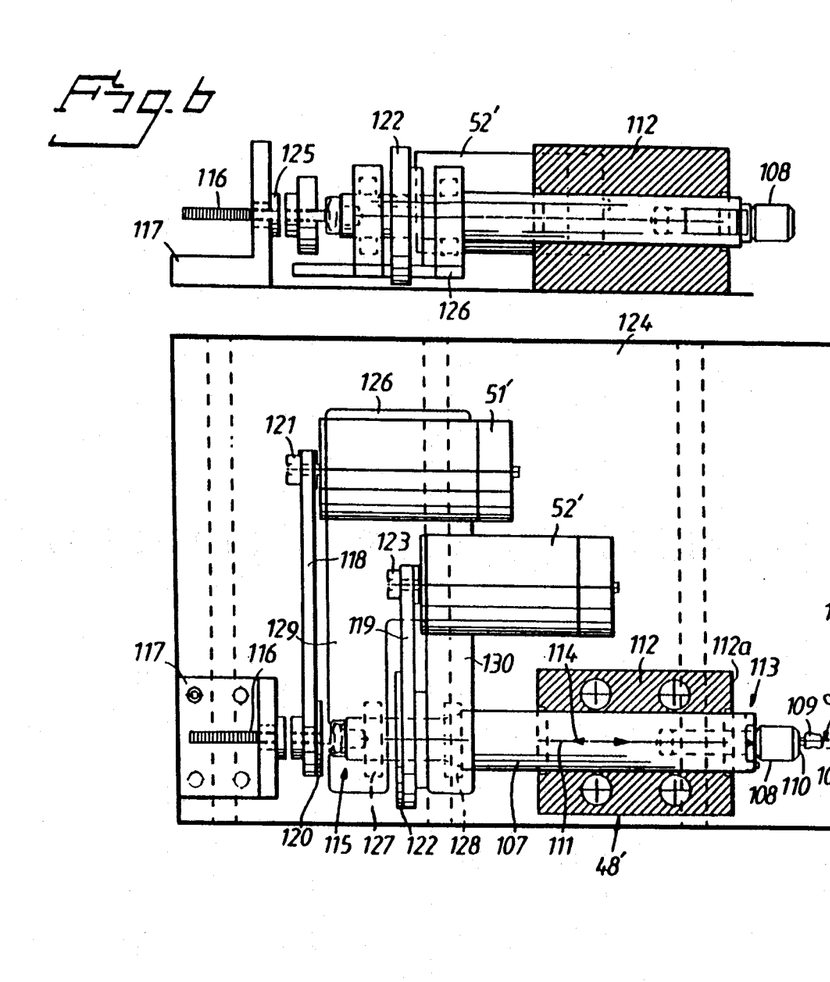
FIG. 6 is a side elevation showing parts of the apparatus according to FIG. 5.
Figure 7:
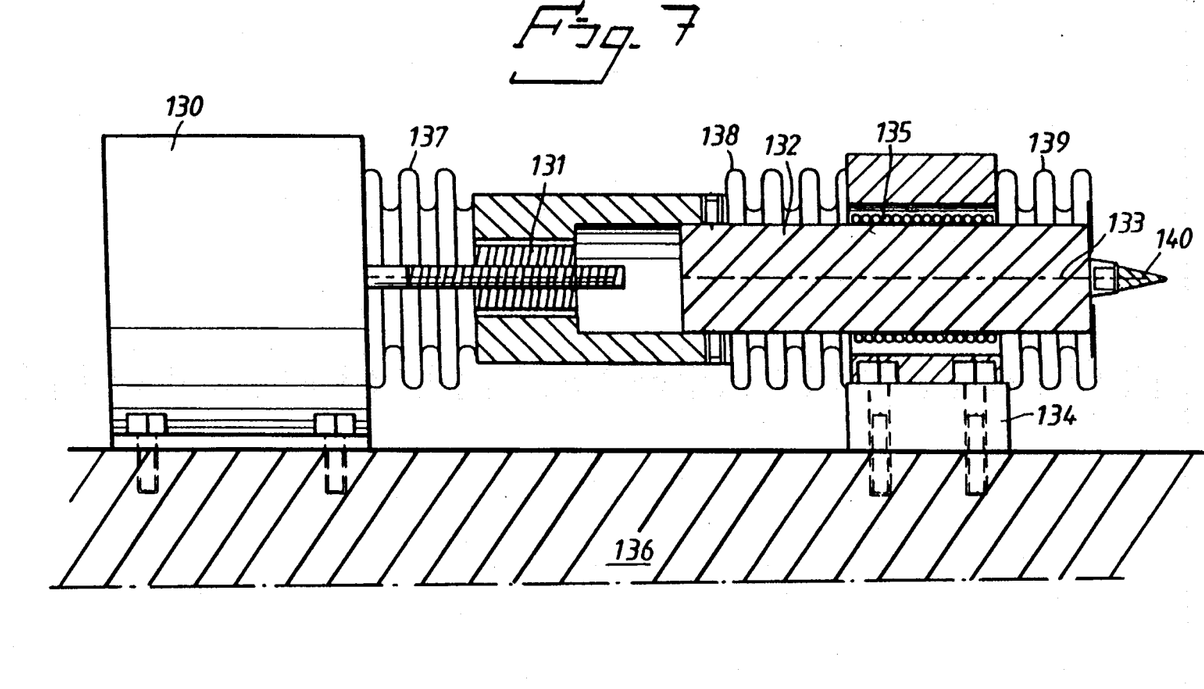
FIG. 7 is a side elevation showing a slightly modified embodiment of parts of the apparatus according to FIG. 5.

FIGS. 5–7 show the blank and tool-supporting units 48' and 49', respectively, in greater detail. There are extreme demands on flexurally rigid support of the movable parts in the units. This is because the materials which are to undergo cutting processing are generally extremely hard (extreme processing forces). In addition, such processing must take place with a high degree of sensitivity and accuracy. In FIG. 5, the switch actuator of the unit 49' has been indicated by reference 93. The switch actuator must be of the type which is electrically controllable with the aid of the above-mentioned signals which are primarily intended to be of the digital type. In one embodiment, the switch actuator may consist of an electrically controlled hydraulic valve which is capable of rapidly controlling an oil flow. The switch actuator includes a return-connected position sensor in its cylinder and is capable of generating a counterforce which is necessary in the cutting process. It must further be able to effectuate variations of about 20 Hz with a high degree of accuracy which gives the contemplated manufacturing accuracy in the body in question. This accuracy is of approximately the 0.01 mm. The switching force must be large in the switch actuator and the mass which is to be displaced by the above-mentioned 20 Hz is of approximately 4 kg. As example of a switch actuator which is applicable in this context, mention may be made of a hydraulic switch actuator of the MOOG brand, type hydraulic cylinder E 851 and an associated electrically switchable valve of the E 769 type. Alternatively, use may be made of a worm gear device as described in connection with FIG. 7 and including a worm gear of SKF make together with a brushless DC motor of, for instance the type MOOG D 313-002A. As an alternative to this motor, use may be made of another rapid acceleration motor. Given that the function and construction of the switch actuator 93 are known, this will not be described in greater detail here. The unit 49' also includes a milling spindle 94 which displays a longitudinally displaceable rotary spindle 95 which is journalled with extreme flexural rigidity with the aid of a ball screw 96. Forwardly, the rotary spindle is provided with an anchorage 97 for a tool 98. As an example of applicable tools, mention may be made of a milling tool. The piston of the cylinder 93 is designated by reference 99, and the spindle 95 is actuated from the piston via a transmission section 100 which includes an angularly inclined portion 101 which projects into a recess 102 in an actuation portion 103 for the spindle 95. The portion 102 actuates the actuation portion 103 in the recess 102 via a ball bearing 104. The spindle is actuated from the actuation portion 103 at its rear regions. At its forward regions, the spindle is rigidly journalled by means of the ball screw 96 along a portion which constitutes approximately half of the total extent of the spindle. This total extent is indicated by reference L, and the above-mentioned portion by reference 1. The longitudinal displacement movements of the spindle along its longitudinal axis 105 are disclosed by the arrows 106. In the figure, the tool 98 has been shown in two different longitudinal displacement positions, the outer longitudinal displacement position having been shown by broken lines with reference 98'. The rotary portion 107 in the unit 48' is also journalled in an extremely flexural rigid manner. The rotary portion 107 carries, at its end, chuck means 108. The blank log is fixedly clampable in the chuck means 108 by means of a bracket 110. In addition to its rotary movement about its longitudinal axis 111, the portion 107 is longitudinally displaceable along its longitudinal axis 111. The blank 109 is shown in two different positions, the outer position being indicated by reference 109'. In this latter position, the above-mentioned co-operation takes place with the tool 98. The rotary portion 107 is journalled in a block 112 via a sliding bearing which is formed by a recess in the block 112. This sliding bearing has a length which is at least half of the length of the portion 107. The portion 107 is disposed with a relatively slight overhang or extremely slight projecting portion 113 from the end surface 112a of the block. The chuck means 108 is permanently secured in the rotary portion 107 in a known manner. The axes 106 and 111 make an obtuse angle α which is preferably selected within the range of between 30° and 60° and, in the illustrated case, is about 45°. In accordance with the above, this angle may be varied within an angular range not specified more closely here, for example an angular range of between 10° and 80° or less. Rotation of the portion 107 is performed by means of the motor 52'. In this instance, the motor is selected so as to to give high speeds of rotation of the rotary portion 107, for example speeds of up to 60,000 rpm. The longitudinal displacement in the direction of the arrows 114 of the portion 107 is realized with the aid of the motor 51'. At the end 115 of the portion 107, a screw 116 is non-rotationally secured, the thread of the screw co-operating with an internal thread in a recess in a block 117. The screw 116 is rotary by means of the motor 51' such that it can be threaded into or out of the recess in the block 117. The portion 107 is, in this instance, disposed to accompany the longitudinal displacement movement of the screw depending on the rotary movements of the screw. The rotary movements of the motors 51' and 52', respectively, are transmitted to the screw and the part 107, respectively, by belt drive 118 and 119, respectively. The screw is fitted with a rotationally fixed wheel 120, and the motor with a drive wheel 121 across which wheels 120 and 121 the belt 118 is laid. Correspondingly, the portion 108 has a non-rotationally disposed belt wheel 122, and the motor 52' a drive wheel 123, over which wheels 122 and 123 the belt 119 is laid. The blocks 112 and 117 are fixedly secured in a frame 124. The recess with the thread which corresponds to the outer thread of the screw is disposed in a bushing-like device 125. The motors 51' and 52' are disposed on a plate 126 which accompanies the longitudinal displacement movement of the portion 107. The motor 51' may rotate at a speed of between 0,5 and 5 rpm. The motors 51' and 52' may consist of stepping motors whose speed is divided into 400 steps. The pitch of the screw 116 is of about 2 mm/turn. At its end 115, the unit is journalled in a fork journal. Two ball bearings 127, 128 are included in this fork bearing. The belt 119 and the belt wheel 122 extend into the space between the fork portions 129 and 130.

FIG. 7 shows a switch actuator in the form of a worm gear device (see 93 in FIG. 5). This so-called worm gear servo includes known parts and will not, be described in detail here. The servo includes a brushless DC motor 130 or servo motor. A worm 131 is rotated in either direction by the motor. A milling spindle 132 is longitudinally displaced in its longitudinal direction along its longitudinal axis 133 depending on rotation of the screw 131. The spindle 132 is journalled in a bearing bracket 134 with rolling bearing arrangement 135. The motor and the bearing bracket are disposed in a block 136. The moving parts are protected by a selector arrangement 137, 138 and 139. This design is also characterized by a high degree of rapidity and extreme switching force. A tool 140 is secured in the end of the spindle. The stations A-D and the stations E-I may form first and second stations disposed on the transmitting and receiving side, respectively, of a communication connection K.

The present invention should not be considered as restricted to the embodiment described above by way of example, many modifications being conceivable without departing from the spirit and scope of the inventive concept as herein disclosed and defined in the appended claims.

What we claim and desire to secure by letters patent is:

1. A method for producing at least one three-dimensional body, said method comprising the steps of:
    a) presetting conditions for sensing at least one model, said conditions including at least an angle of at least one sensor with respect to a longitudinal axis of said model and a relationship between a rotation speed of said model and a speed of movement of said sensor and said model relative to each other in a direction parallel to said longitudinal axis of said model;
    b) rotating said model while simultaneously moving at least one of said model and said sensor relative to each other in a direction parallel to said longitudinal axis of said model while simultaneously sensing a plurality of distances generated by interaction between said sensor and a surface of said model to obtain a first set of data;
    c) transmitting said preset conditions and said first set of data to at least one control means for controlling at least one working tool for producing said three-dimensional bodies;
    d) substantially duplicating said preset conditions of said at least one sensor and said at least one model for at least one working tool and at least one blank respectively; and
    e) producing said three-dimensional body by varying a position of said working tool relative to said blank corresponding to said sensed distance generated by interaction between said sensor and said model, such that said working tool selectively removes material from said blank to substantially reproduce said surface of said model on said blank.

2. A method for producing at least one three-dimensional body according to claim 1, further comprising the steps of:
    f) inputting said first set of data into memory of a computer;
    g) modifying said first set of data to obtain a second set of data, said modification corresponding to a desired modification of said three-dimensional body produced;
    h) generating an output from said computer in the form of a control signal;
    i) transmitting said control signal to said means for controlling said working tool; and
    j) producing a three-dimensional body including a surface different from said surface of said model.

3. A method for producing at least one three-dimensional body according to claim 1, wherein the entire surface of said model is sensed in one continuous motion.

4. A method for producing at least one three-dimensional body according to claim 1, further comprising the steps of:
    f) altering at least one of said preset conditions at a point during said interaction between said sensor and said surface of said model;
    g) transmitting said alteration of said at least one preset condition to said control means; and
    h) duplicating said alteration of said at least one preset condition in said working tool and said blank at a point during the production of said three-dimensional body corresponding to said point during said interaction between said sensor and said surface of said model.

5. A method for producing at least one three-dimensional body according to claim 1, further comprising the steps of:
    f) inputting said first set of data into memory of a computer;
    g) creating a graphic representation of said first set of data on a display of said computer;
    h) altering said graphic representation on said display, thereby producing a second set of data;
    i) transmitting said second set of data to said control means; and
    j) producing said three-dimensional body by varying a position of said working tool relative to said blank corresponding to said second set of data, such that said working tool selectively removes material from said blank to produce a surface on said blank.

6. A method for producing at least one three-dimensional body according to claim 1, further comprising the step of conveying said first set of data to said means for controlling said working tool over a transmission line temporarily or permanently connected to a public communications network, wherein said first set of data is transmitted and received by modems.

7. A method for producing at least one three-dimensional body according to claim 2, wherein said modification includes enlargement or reduction of said surface of said model or alteration of a portion of the surface of the model.

8. A method for producing at least one three-dimensional body according to claim 1, further comprising the steps of:
    f) storing said preset conditions and said first set of data on a portable storage medium after being sensed;
    g) reading said preset conditions and said first set of data from said portable storage medium; and
    h) transmitting said preset conditions and said first set of data to said means for controlling said working tool with said portable storage medium.

9. A method for producing at least one three-dimensional body according to claim 1, wherein said three-dimensional body is a tooth implant, tooth replacement, tooth crown, prosthesis, or construction part of a prosthesis.

10. A method for producing at least one three-dimensional body according to claim 1, wherein said rotation speed of said blank as said three-dimensional body is produced is substantially similar to said rotation speed of said model as said sensor interacts with said model.

11. A method for producing at least one three-dimensional body according to claim 1, wherein said speed of movement of said sensor and said model relative to each other in a direction parallel to said longitudinal axis of said model is substantially similar to the movement of said blank and said working tool relative to each other in a direction parallel to the longitudinal axis of said blank.

12. An apparatus for producing at least one three-dimensional body, said apparatus comprising:

at least one sensor for sensing at least one model;

means for presetting conditions for sensing the model, said conditions including at least an angle of the sensor with respect to a longitudinal axis of the model and a relationship between a rotation speed of the model and a speed of movement of said sensor and the model relative to each other in a direction parallel to said longitudinal axis of the model;

means for rotating the model while simultaneously moving at least one of the model and the sensor relative to each other in a direction parallel to a longitudinal axis of the model and while said sensor simultaneously senses a plurality of distances generated by interaction between said sensor and a surface of the model to obtain a first data set;

at least one means for transmitting said preset conditions and said first set of data to means for controlling a working tool;

means for substantially duplicating said preset conditions for said sensor and the model in a working tool and a blank, respectively;

at least one working tool for removing material from at least one blank to produce said at least one three-dimensional body; and at least one means for controlling said working tool to vary the position of said working tool relative to the blank, said position of said working tool corresponding to the distances generated by interaction between said sensor and the model, such that said working tool selectively removes material from the blank to substantially reproduce on the blank the surface of the model.

13. An apparatus for producing at least one three-dimensional body according to claim 12, wherein said sensor is a contact sensor.

14. An apparatus for producing at least one three-dimensional body according to claim 12, wherein said sensor is a laser sensor.

15. An apparatus for producing at least one three-dimensional body according to claim 12, further comprising a computer for receiving said first set of data, for altering said first set of data and transmitting said data to said means for controlling said working tool thereby altering said three-dimensional body produced.

16. An apparatus for producing at least one three-dimensional body according to claim 12, further comprising means for altering at least one of said preset conditions at a point during said interaction between said sensor and said surface of said model, for transmitting said alteration of said preset conditions to said means for controlling said working tool, and for duplicating said alteration of said at least one of said preset conditions in said working tool and said blank at a point during the production of said three-dimensional body corresponding to said point during said interaction between said sensor and said surface of said model.

17. An apparatus for producing at least one three-dimensional body according to claim 15, further comprising means for creating a graphic representation of said first data set on a display of said computer and for altering said graphic representation on said display thereby producing a second set of data and means for transmitting said second set of data to said means for controlling said working tool.

18. An apparatus for producing at least one three-dimensional body according to claim 12, wherein said transmitting means is a modem for transmitting said first set of data connected to a public telephone line and a modem for receiving said first set of data and transmitting said first set of data to said means for controlling said working tool.

19. An apparatus for producing at least one three-dimensional body according to claim 12, further comprising a floppy disk drive for storing said first set of data.

* * * * *